United States Patent [19]

Meli et al.

[11] 4,185,124
[45] Jan. 22, 1980

[54] 2-(4-BIPHENYLYL)-N-(2-DIETHYLAMINO ALKYL)PROPIONAMIDE AND SALTS THEREOF USED AS SPASMOLYTIC AGENTS

[75] Inventors: Alberto Meli; Claudio Bianchini; Piero del Soldato; Mario Ghelardoni; Vittorio Pestellini; Giovanna Volterra, all of Florence, Italy

[73] Assignee: A. Menarini S.A.S., Italy

[21] Appl. No.: 905,006

[22] Filed: May 11, 1978

[51] Int. Cl.$^2$ .................. A61K 31/165; C07C 103/20
[52] U.S. Cl. .................. 424/324; 260/558 R
[58] Field of Search .................. 260/558 R; 424/324

[56] References Cited

U.S. PATENT DOCUMENTS 3,859,338  1/1975  Engel et al. .................. 260/558 R X

OTHER PUBLICATIONS

G. Cavallini et al., Farm. Sci. Tech. 3, 648 (1948).

*Primary Examiner*—Leonard Schenkman
*Attorney, Agent, or Firm*—McGlew and Tuttle

[57] ABSTRACT

New compounds useful as spasmolytic agents are provided with the following formula:

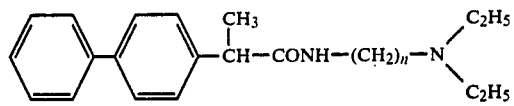

wherein n is either 2 or 3. In addition, salts of these new compounds are provided and are suitable for oral as well as parenteral administration to animals and man as spasmolytic agents. In compositions for oral and parenteral or rectal administration, from about 5 to about 40 mg of active ingredient per dosage unit is used. The bromide and iodide salts of these new compounds are especially useful.

21 Claims, No Drawings

2-(4-BIPHENYLYL)-N-(2-DIETHYLAMINO ALKYL)PROPIONAMIDE AND SALTS THEREOF USED AS SPASMOLYTIC AGENTS

BACKGROUND OF THE INVENTION

1. Field of the Invention

The present invention is concerned with new compounds having high spasmolytic action. More particularly, the invention relates to certain propionamide derivatives, their pharmaceutically acceptable salts and methods of using these compounds as spasmolytic agents in man and animals.

2. Prior Art

Among the products usually employed in therapy as spasmolytic, it is frequently observed that the action of some of these known products is confined to the gastrointestinal tract. Those products that after oral administration exert their action also on organs and systems other than the gastrointestinal tract, however, have atropine like side effects.

SUMMARY OF THE INVENTION

It has been found that the new compounds of the general formula I:

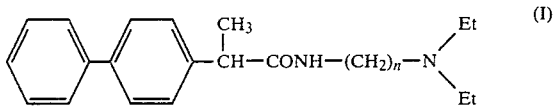

wherein n is 2 or 3, and Et is the ethyl group, $C_2H_5-$, and their non-toxic, pharmaceutically acceptable salts are particularly suitable for oral or parenteral use. These new compounds and their salts differ from the already known products because: (a) inhibit the transmission of the nervous impulse to the muscular fiber (parasympatholytic activity); (b) inhibit the contraction of the smooth musculature (direct myolytic activity); and (c) have lower side effects on the central and peripheral nervous system.

It has been found that the new compounds corresponding to the general formula I and their non-toxic salts are particularly suitable for oral as well as parenteral use and differ from the already known products for their direct parasympatholytic and myolytic activity and for their lower side effects on the central and peripheral nervous system. Specific examples of compounds related to the formula I are:
(1) 2-(4-biphenyl)-N-(2-diethylaminoethyl) propionamide; and
(2) 2-(4-biphenyl)-N-(3-diethylaminopropyl) propionamide.

The bromide and iodide salts of (1) and (2) are especially useful as spasmolytic agents.

Pharmaceutically acceptable salts of the above mentioned compounds are, for instance, the non-toxic chloride, bromide, iodide, phosphate, and sulphate salts, as well as the methyl bromide, methyl iodide, ethyl bromide, ethyl iodide salts.

Compounds of the formula I are prepared according to known methods. In particular, these compounds are made by reacting a functional derivative of 2-(4-biphenyl) propionic acid with N,N-diethylethylenediamine or N,N-diethyl-1,3-propylenediamine in the presence of a suitable solvent. As functional derivative of 2-(4-biphenyl)propionic acid the chloride or the corresponding anhydride of said acid is very useful as well as an ester of the same acid and, in particular, a lower alkyl ester such as the methyl ester of said acid. Using the chloride of the acid as reagent, it is preferable to perform the condensation reaction with N,N-diethylethylenediamine or N,N-diethyl-1,3-propylenediamine in the presence of a base.

The salts of the compounds of the formula I are also prepared according to known methods. The alkylhalogen derivatives are prepared by alkylation of the bases according to formula I, with alkylating agents such as alkyl chloride, alkyl bromide or alkyl iodide in an organic low boiling solvent, including, for example, dioxane, acetone, ethyl ether.

EXAMPLE 1

Preparation of 2-(4-biphenyl)-N-(2-diethylamino ethyl) propionamide

To 11.6 g of N,N-diethylethylenediamine in 60 ml of benzene are slowly added dropwise, with stirring, 24.4 g of 2-(4-biphenyl)-propionic acid chloride dissolved in 60 ml of benzene. After 1 hour refluxing, the mixture is concentrated, extracted with ethyl ether and water, and precipitation occurs from the aqueous solution with soda; crystallization of the desired product follows from hexane: melting point 67°–68° C.

I.R. (Nujol), $\nu$ max (cm$^{-1}$): 3340 (NH), 1640 (CO)

H-NMR (CCl$_4$), $\delta$ (ppm): 1 (t, 2 x CH$_3$) 1.6 (d,CH$_3$) 2.3–2.6 (m, 3 x CH$_2$) 3.3 (q, CH$_2$) 3.6 (q, CH) 7.2–7.5 (m, C$_6$H$_4$ and C$_6$H$_5$).

EXAMPLE 2

Preparation of 2-(4-biphenyl)-N-(3-diethylaminopropyl) propionamide

To 13 g of N,N-diethyl-1,3-propylenediamine in 60 ml of benzene are slowly added dropwise, with stirring, 24.4 g of 2-(4-biphenyl) propionic acid chloride dissolved in 60 ml of benzene. After 2 hours refluxing, the mixture is concentrated, extracted with ethyl ether and water; precipitation occurs with soda from the aqueous solution, crystallization of the desired product follows from hexane: m.p. 44°–45° C.

I.R. (Nujol), $\nu$ max (cm$^{-1}$): 3280 (NH), 1640 (CO)

H-NMR (CDCl$_3$), $\delta$ (ppm): 1.1 (t, 2 x CH$_3$) 1.6–1.9 (m, CH$_3$ and CH$_2$) 2.4–2.7 (m, 3 x CH$_2$) 3.5 (q, CH$_2$) 3.8 (q, CH) 7.5–7.9 (m, C$_6$H$_4$ and C$_6$H$_5$).

EXAMPLE 3

Preparation of 2-(4-biphenyl)-N-(2-diethylmethylammonium-ethyl) propionamide bromide.

In 8 g of 2-(4-biphenyl)-N-(2-diethylamino-ethyl) propionamide dissolved in 20 ml of acetone 2.5 g of methyl bromide are bubbled. The precipitate is filtered and crystallized from isopropyl alcohol: m.p. 161°–163° C.

I.R. (Nujol) $\nu$ max (cm$^{-1}$): 3150 (NH), 1650 (CO)

H-NMR (CDCl$_3$), $\delta$ (ppm): 1.3 (t, 2 x CH$_3$) 1.6 (d, CH$_3$) 3.2 (s, CH$_3$) 3.4–4.0 (m, 4x CH$_2$ and CH) 7.4–7.7 (m, C$_6$H$_4$ and C$_6$H$_5$).

EXAMPLE 4

Preparation of 2-(4-biphenyl)-N-(3-diethylmethyl-ammonium propyl) propionamide bromide.

In 8.5 g of 2-(4-biphenyl)-N-(3-diethylaminopropyl) propionamide dissolved in 20 ml of acetone 2.5 g of methyl bromide are bubbled. The precipitate is filtered and crystallized from acetone/ethyl ether; the melting point of the desired product is 116°-118° C. and this product is characterized as follows:

I.R. (Nujol), $\nu$ max (cm$^{-1}$): 3150 (NH), 1645 (CO)
H-NMR (CDCl$_3$), δ (ppm): 1.25 (t, 2 x CH$_3$), 1.55 (d, CH$_3$) 1.8–2.3 (m, CH$_2$) 3 (s, CH$_3$) 3.1–3.7 (m, 4 x CH$_2$) 3.7–4.2 (q, CH) 7.4–7.7 (m, C$_6$H$_4$ and C$_6$H$_5$).

EXAMPLE 5

Preparation of 2-(4-biphenyl)-N-(2-diethylmethyl-ammoniumethyl) propionamide iodide.

To 8.0 g of 2-(4-biphenyl)-N-(2-diethylaminoethyl) propionamide dissolved in 25 ml of ethyl alcohol 4 g of methyl iodide are added. The mixture is dried under vacuum and crystallized from acetone: yielding the desired product whose melting point is 132°-134° C. This product has the following characteristic properties:

I.R. (Nujol) $\nu$ max (cm$^{-1}$): 3200 (NH), 1655 (CO)
H-NMR (CDCl$_3$), δ (ppm): 1.3 (t, 2x CH$_3$) 1.6 (d, CH$_3$) 3.1 (s, CH$_3$) 3.3–4.0 (m, 4 x CH$_2$ and CH) 7.4–7.65 (m, C$_6$H$_5$ and C$_6$H$_4$).

EXAMPLE 6

Biologic Activity: Use of Formula I compounds as spasmolytic agents in animals The potential myolytic activity of the compounds of the present invention was determined by measuring the transit of a charcoal meal in mouse intestine, stimulated by BaCl$_2$, according to P. A. J. Janssen and A. Jageneau, *J. Pharm. Pharmacol.* 9, 381, 1957.

The potential parasympatholytic activity of the compounds of the present invention was tested by evaluating in the anesthetized guinea pig their antagonism toward the carbachol induced bronchoconstriction (according to M. E. Rosenthale and A. Pervinis, *Arch. Int. Pharmacodyn.* 1, 172, 1968), and bradycardia and hypotension (according to J. P. Long and C. Y. Chiou, *J. Pharm. Sciences* 59, 133, 1970).

The results are reported in the following Table 1.

Table 1

| Compound | Inhibition of BaCl$_2$ stimulation of intestinal peristalsis (Charcoal meal) Potency ratio. | Anaesthetized guinea pig. Inhibition of the following effect induced by carbachol* (Potency ratio) | | |
|---|---|---|---|---|
| | | Bronchoconstriction | Hypotension | Bradycardia |
| 1 | 0.9 | 0.2 | 5 | 0.2 |
| 2 | 1.5 | 1 | 10 | 1.4 |
| 3 | 1.9 | 0.9 | 10 | 1.2 |
| Dicyclomine HCl | 9 | 1 | 1 | 1 |

*The compounds were administered intraduodenally at a dose of 25 mg/Kg. Carbachol (5 μg/Kg) was administered intravenously before and 40 minutes after the administration of test compounds.
Compound 1 = 2-(4-biphenyl)-N-(2-diethylaminoethyl) acetamide
Compound 2 = 2-(4-biphenyl)-N-(2-diethylaminoethyl) propionamide
Compound 3 = 2-(4-biphenyl)-N-(3-diethylaminopropyl) propionamide These results clearly indicate that presence of the propionamide structure is required to better spasmolytic activity. In fact the already known 2-(4-biphenyl)-N-(2-diethylaminoethyl) acetamide Cavallini, F. Ravenna *Farm. Sci. Tecn.* 3, 648 (1948) has a direct parasympatholytic and myolytic activity definitely lower than that of 2-(4-biphenyl)-N-(2-diethylaminoethyl) propionamide. Furthermore, this latter is 1.5 times as effective as dicyclomine in antagonizing smooth muscle contraction (direct myolytic effect) and 10 times as effective as dicyclomine in antagonizing the transmission of the nervous impulses to the muscular fiber (parasympatholytic effect).

The atropinelike side effects of these compounds have been studied with the oxotremorine test according to the method described by Leslie G., Hayman G., Ireson J. D. and Smith S., *Arch. Int. Pharmacodyn.* 197, 108, 1972, evaluating the central effects (tremors) and peripheral effects (salivation, lacrimation, diarrhea) and with the apomorphine test according to the method described by J. Scheel-Krüger, *Acta Pharmacol. Toxicol.* 28, 1, 1970, evaluating the central anticholinergic activity. The data are reported in Table 2.

TABLE 2

| Central anticholinergic activity Potentiation of apomorphine effects according to Scheel-Krüger[a] | | Central and peripheral effects. Inhibition of oxotremorine effects[b] | |
|---|---|---|---|
| Compounds | Activity index | Compounds | Activity index |
| Dicyclomine HCl | 1 | Dicyclomine HCl | 1 |
| 2[c] | 0.5 | 2[c] | 0.2 |
| Atropine sulphate | 1.3 | Scopolamine butyl bromide | 1.2 |

[a]Average effect of 3 doses (30–60–90 mg/Kg/os) of the compounds administered to female mice (17–25 g) 1 hour before apomorphine (10 mg/Kg/s.c.). The gnawing intensity is evaluated for the products and the control (H$_2$O) for a 40 minute period.
[b]Average effect of 3 doses (28.6–57.2–114.4 mg/Kg/os) of the compounds administered to male mice (18–25 g) 1 hour before oxotremorine (0.5 mg/Kg/s.c.). The effect on lacrimation, salivation, diarrhea and tremor in comparison with controls (H$_2$O) is evaluated in 15–30–60 and 120 min. after oxotremorine.
Compound 2[c] = 2-(4-biphenyl)-N-(2-diethylaminoethyl) propionamide It is seen from Table 2 that in comparison with 2-(4-biphenyl)-N-(2-diethylaminoethyl) propionamide, dicyclomine and scopolamine butyl bromide have respectively 5 or 6 times higher central and peripheral side-effects. As to the central anticholinergic activity, dicyclomine and atroine sulphate have about 2 times higher side-effects in relation to 2-(4-biphenyl)-N-(2-diethylaminoethyl) propionamide.

None of the mentioned products exhibits anti-phlogistic property as determined by the carrageenan paw edema test according to Winter, E. A., Risley, E. A. and Nuss, G. W., *Proc. Soc. Exp. Biol. Med.* 111, 544, 1962.

The present invention further provides pharmaceutical compositions comprising at least one compound of formula I in association with a pharmaceutical carrier or excipient. The pharmaceutical composition may be presented in a form suitable, for example, for oral or parenteral or rectal administration in dosis ranging from 5 to 40 mg of active ingredients.

Examples of suitable forms of administration include, vials, tablets, coated tablets, capsules, lozenges, dispersible powders, syrups and elixers. Preferably the compositions are presented in dosage unit form.

What is claimed is:

1. A member selected from the group consisting of
(a) a compound of the formula

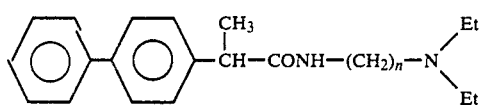

wherein n is 2 or 3, and Et is $C_2H_5$, and
(b) the non-toxic salts of (a).

2. Compound according to claim 1, which is 2-(4-biphenyl)-N-(2-diethylaminoethyl)propionamide.

3. Compound according to claim 1, which is 2-(4-biphenyl)-N-(2-diethylaminopropyl) propionamide.

4. Compound according to claim 1, which is 2-(4-biphenyl)-N-(2-diethylmethylammonium-ethyl) propionamide halide.

5. Compound according to claim 1, which is 2-(4-biphenyl)-N-(2-diethylmethylammonium-propyl)propionamide halide.

6. Compound according to claim 1, which is 2-(4-biphenyl)-N-(2-diethylmethylammonium-ethyl)propionamide bromide.

7. Compound according to claim 1, which is 2-(4-biphenyl)-N-(2-diethylmethylammonium-propyl)propionamide bromide.

8. Compound according to claim 1, which is 2-(4-biphenyl)-N-(2-diethylmethylammonium-ethyl)propionamide iodide.

9. Compound according to claim 1, which is 2-(4-biphenyl)-N-(2-diethylmethylammonium-propyl)propionamide iodide.

10. Compound according to claim 1, which is 2-(4-biphenyl)-N-(2-diethylmethylammonium-ethyl)propionamide chloride.

11. Compound according to claim 1, which is 2-(4-biphenyl)-N-(2-diethylmethylammonium-propyl)propionamide chloride.

12. Compound according to claim 1, which is 2-(4-biphenyl)-N-(2-diethylmethylammonium-ethyl)propionamide sulphate.

13. Compound according to claim 1, which is 2-(4-biphenyl)-N-(2-diethylmethylammonium-propyl)propionamide sulphate.

14. Compound according to claim 1, which is 2-(4-biphenyl)-N-(2-diethylmethylammonium-ethyl)propionamide phosphate.

15. Compound according to claim 1, which is 2-(4-biphenyl)-N-(2-diethylmethylammonium-propyl)propionamide phosphate.

16. Pharmaceutical composition wherein said composition comprises a non-toxic, inert vehicle or carrier, and a spasmolytic agent comprising a member selected from the group consisting of
(a) a compound of the formula

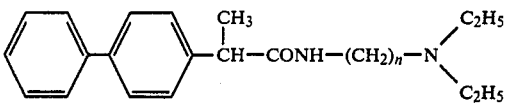

wherein n is 2 or 3, and
(b) the non-toxic salts of (a), said spasmolytic agent being employed in dosage units ranging from about 5 to about 40 mg.

17. Pharmaceutical composition according to claim 16, wherein said compound (a) comprises 2-(4-biphenyl)-N-(2-diethylaminoethyl)propionamide.

18. Pharmaceutical composition according to claim 16, wherein said compound (a) comprises 2-(4-biphenyl)-N-(2-diethylaminopropyl)propionamide.

19. Pharmaceutical composition according to claim 16, wherein said compound (b) comprises 2-(4-biphenyl)-N-(2-diethylmethyl ammonium ethyl)propionamide bromide.

20. Pharmaceutical composition according to claim 16, wherein said compound (b) comprises 2-(4-biphenyl)-N-(2-diethyl-methylammonium propyl)propionamide bromide.

21. Pharmaceutical composition according to claim 16, wherein said compound (b) comprises 2-(4-biphenyl)-N-(2-diethyl-methylammonium ethyl)propionamide iodide.

* * * * *